(12) United States Patent
Jin et al.

(10) Patent No.: US 7,483,809 B2
(45) Date of Patent: Jan. 27, 2009

(54) OPTICAL METROLOGY USING SUPPORT VECTOR MACHINE WITH PROFILE PARAMETER INPUTS

(75) Inventors: Wen Jin, Sunnyvale, CA (US); Junwei Bao, Palo Alto, CA (US); Shifang Li, Pleasanton, CA (US)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 11/786,869

(22) Filed: Apr. 12, 2007

(65) Prior Publication Data

US 2008/0255786 A1 Oct. 16, 2008

(51) Int. Cl.
*G01B 5/20* (2006.01)
(52) U.S. Cl. ............................ 702/167; 702/119; 702/182
(58) Field of Classification Search .................. 703/119, 703/14; 702/182, 189, 31, 66, 12, 21; 356/625, 356/73
See application file for complete search history.

(56) References Cited

U.S. PATENT DOCUMENTS

| | | |
|---|---|---|
| 5,479,573 A | 12/1995 | Keeler et al. |
| 5,793,480 A | 8/1998 | Lacey et al. |
| 5,889,593 A | 3/1999 | Bareket |
| 6,023,327 A | 2/2000 | Shabde et al. |
| 6,192,103 B1 | 2/2001 | Wormington et al. |
| 6,609,086 B1 | 8/2003 | Bao et al. |
| 6,633,831 B2 | 10/2003 | Nikoonahad et al. |
| 6,650,422 B2 | 11/2003 | Singh et al. |
| 6,657,736 B1 | 12/2003 | Finarov et al. |
| 6,665,446 B1 | 12/2003 | Kato |
| 6,704,661 B1 | 3/2004 | Opsal et al. |
| 6,771,356 B1 | 8/2004 | Lyons et al. |
| 6,782,337 B2 | 8/2004 | Wack et al. |

(Continued)

FOREIGN PATENT DOCUMENTS

EP 0448890 A1 10/1991

OTHER PUBLICATIONS

Platt, J. C. (1999). "Fast Training of Support Vector Machines Using Sequential Minimal Optimization" Chapter 12 *In Advances in Kernel Methods: Support Vector Learning.* Schölkopf et al. eds., MIT Press: Cambridge, MA, pp. 185-208.

(Continued)

*Primary Examiner*—Eliseo Ramos Feliciano
*Assistant Examiner*—Mi'schita' Henson
(74) *Attorney, Agent, or Firm*—Morrison & Foerster LLP (57) ABSTRACT

A structure formed on a semiconductor wafer can be examined using a support vector machine. A profile model is defined by profile parameters that characterize the geometric shape of the structure. A training set of values for the profile parameters is obtained. A training set of simulated diffraction signals is generated using the training set of values for the profile parameters. The support vector machine is trained using the training set of values for the profile parameters. A simulated diffraction signal is generated using a set of values for the profile parameters as inputs to the trained support vector machine. A measured diffraction signal is compared to the simulated diffraction signal. When the signals match within one or more matching criteria, values of profile parameters of the structure are determined to be the set of values for the profile parameters used to generate the simulated diffraction signal.

21 Claims, 9 Drawing Sheets

U.S. PATENT DOCUMENTS

| | | | |
|---|---|---|---|
| 6,785,638 | B2 | 8/2004 | Niu et al. |
| 6,943,900 | B2 | 9/2005 | Niu et al. |
| 6,999,254 | B1 | 2/2006 | Phan et al. |
| 7,043,397 | B2 | 5/2006 | Johnson |
| 7,072,049 | B2 | 7/2006 | Niu et al. |
| 7,092,110 | B2 | 8/2006 | Balasubramanian et al. |
| 7,126,700 | B2 | 10/2006 | Bao et al. |
| 7,158,896 | B1 | 1/2007 | Singh et al. |
| 7,186,650 | B1 | 3/2007 | Dakshina-Murthy |
| 7,216,045 | B2 | 5/2007 | Doddi et al. |
| 7,224,456 | B1 | 5/2007 | Phan et al. |
| 7,224,471 | B2 | 5/2007 | Bischoff et al. |
| 7,280,229 | B2 | 10/2007 | Li et al. |
| 2003/0187604 | A1* | 10/2003 | Drege et al. ............ 702/119 |
| 2004/0017574 | A1 | 1/2004 | Vuong et al. |
| 2004/0267397 | A1 | 12/2004 | Doddi et al. |
| 2005/0057748 | A1 | 3/2005 | Vuong et al. |
| 2005/0192914 | A1 | 9/2005 | Drege et al. |
| 2005/0209816 | A1 | 9/2005 | Vuong et al. |
| 2006/0224528 | A1 | 10/2006 | Liu et al. |
| 2007/0185684 | A1 | 8/2007 | Vuong et al. |

OTHER PUBLICATIONS

Keeman, V. (2005). "Support Vector Machine—An Introduction" In *Support Vector Machines: Theory and Applications.* Wang, L. ed., Springer-Verlag Berlin Heidelberg: The Netherlands, pp. 1-47.

U.S. Appl. No. 11/349,773, filed Feb. 7, 2006 for Vuong et al.

U.S. Appl. No. 11/786,870, filed Apr. 12, 2007 for Jin et al.

U.S. Appl. No. 11/787,025, filed Apr. 12, 2007 for Jin et al.

Arthur, G. G. et al. (1997). "Enhancing the Development Rate Model for Optimum Simulation Capability in the Subhalf-Micron Regime," *Proceedings of SPIE* 3049:189-200.

Brooks, R. A. (1999). "How to Build Complete Creatures Rather than Isolated Cognitive Simulators," MIT, Artificial Intelligence Laboratory, 7 pages, located at <http://people.csail.mit.edu/brooks/papers/how-to-build.pdf>.

Del Jesus, M. J. et al. (Jun. 2004). "Induction of Fuzzy-Rule-Based Classifiers with Evolutionary Boosting Algorithms," *IEEE Transactions on Fuzzy Systems* 12(3):296-308.

Dietterich, T. G. (1997). Machine Learning Research: Four Current Directions, *AI Magazine,* pp. 97-136, located at <http://pages.cs.wisc.edu/~shavlik/Dietterich_AIMag 18-04-010.pdf>.

Gahegan, M. et al. (1999). "Dataspaces as an Organizational Concept for the Neural Classification of Geographic Datasets," GeoComputation, located at <http://www.geovista.psu.edu/sites/geocomp99/Gc99/011/gc_011.htm> visited on Aug. 14, 2007, (8 pages).

Goodridge, S. G. et al. (May 8-13, 1994). "Fuzzy Behavior Fusion for Reactive Control of an Autonomous Mobile Robot: MARGE," *IEEE International Conference on Robotics and Automation,* San Diego, CA, 2:1622-1627.

Haykin, S. (1999). *Neural Networks.* 2nd edition, M. Horton ed., Prentice Hall: Upper Saddle River, New Jersey, 9 pages (Table of Contents).

Horswill, I. D. (2000). "Conflict Resolution," Northwestern University, Computer Science 395 Behavior-Based Robotics, 10 pages, located at <www.cs.northwestern.edu/academics/courses/special_topics/395-robotics/conflict-resolution.pdf>.

Horswill, I. D. (2000). "Functional Programming of Behavior-Based Systems," Northwestern University, Computer Science Department and The Institute for the Learning Sciences, 11 pages, <www.cs.northwestern.edu/~ian/grl-paper.pdf>.

International Search Report and Written Opinion mailed May 16, 2005, for PCT Application No. PCT/US04/20682 filed Jun. 25, 2004, 7 pages.

Press, W. H. et al. (1992). *Numerical Recipes in C: The Art of Scientific Computing.* Cambridge University Press, 2nd edition, 8 pages (Table of Contents).

Rowe, N. C. (1990). "Plan Fields and Real-World Uncertainty," *AAAI Spring Symposium on Planning in Uncertain, Unpredictable, or Changing Environments,* located at <http://www.nps.navy.mil/Content/CS/ncrowe/symp90un.html> visited on Oct. 18, 2007. (4 pages).

Sarkar, M. (Oct. 8-11, 2000). "Modular Pattern Classifiers: A Brief Survey," *IEEE International Conference on Systems, Man & Cybernetics,* Nashville, TN, 4:2878-2883.

U.S. Appl. No. 11/729,498, filed Mar. 28, 2007 for Bischoff et al.

Van Halteren, H. et al. (Jun. 2001). "Improving Accuracy in World Class Tagging Through Combination of Machine Learning Systems," *Computational Linguistics* 27(2):199-229.

Vapnik, V. N. (1998). *Statistical Learning Theory.* John Wiley & Sons, Inc., 15 pages (Table of Contents).

\* cited by examiner

OPTICAL METROLOGY USING SUPPORT VECTOR MACHINE WITH PROFILE PARAMETER INPUTS

BACKGROUND

1. Field

The present application generally relates to optical metrology of structures formed on semiconductor wafers, and, more particularly, to optical metrology using a support vector machine with profile parameter inputs.

2. Related Art

Optical metrology involves directing an incident beam at a structure, measuring the resulting diffracted beam, and analyzing the diffracted beam to determine a feature of the structure. In semiconductor manufacturing, optical metrology is typically used for quality assurance. For example, after fabricating a periodic grating in proximity to a semiconductor chip on a semiconductor wafer, an optical metrology system is used to determine the profile of the periodic grating. By determining the profile of the periodic grating, the quality of the fabrication process utilized to form the periodic grating, and by extension the semiconductor chip proximate the periodic grating, can be evaluated.

One conventional optical metrology system uses a diffraction modeling technique, such as rigorous coupled wave analysis (RCWA), to analyze the diffracted beam. More particularly, in the diffraction modeling technique, a model diffraction signal is calculated based, in part, on solving Maxwell's equations. Calculating the model diffraction signal involves performing a large number of complex calculations, which can be time consuming and costly.

SUMMARY

In one exemplary embodiment, a structure formed on a semiconductor wafer can be examined using a support vector machine. A profile model of the structure is obtained. The profile model is defined by profile parameters that characterize the geometric shape of the structure. A training set of values for the profile parameters is obtained. A training set of simulated diffraction signals is generated using the training set of values for the profile parameters, each simulated diffraction signal characterizing the behavior of light diffracted from the structure. The support vector machine is trained using the training set of values for the profile parameters as inputs to the support vector machine and the training set of simulated diffraction signals as expected outputs of the support vector machine. A measured diffraction signal off the structure is obtained. A simulated diffraction signal is generated using a set of values for the profile parameters as inputs to the trained support vector machine. The measured diffraction signal is compared to the simulated diffraction signal. When the measured diffraction signal and simulated diffraction signal match within one or more matching criteria, values of profile parameters of the structure are determined to be the set of values for the profile parameters used to generate the simulated diffraction signal.

DESCRIPTION OF DRAWING FIGURES

The present invention can be best understood by reference to the following description taken in conjunction with the accompanying drawing figures, in which like parts may be referred to by like numerals.

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

Figure 1:
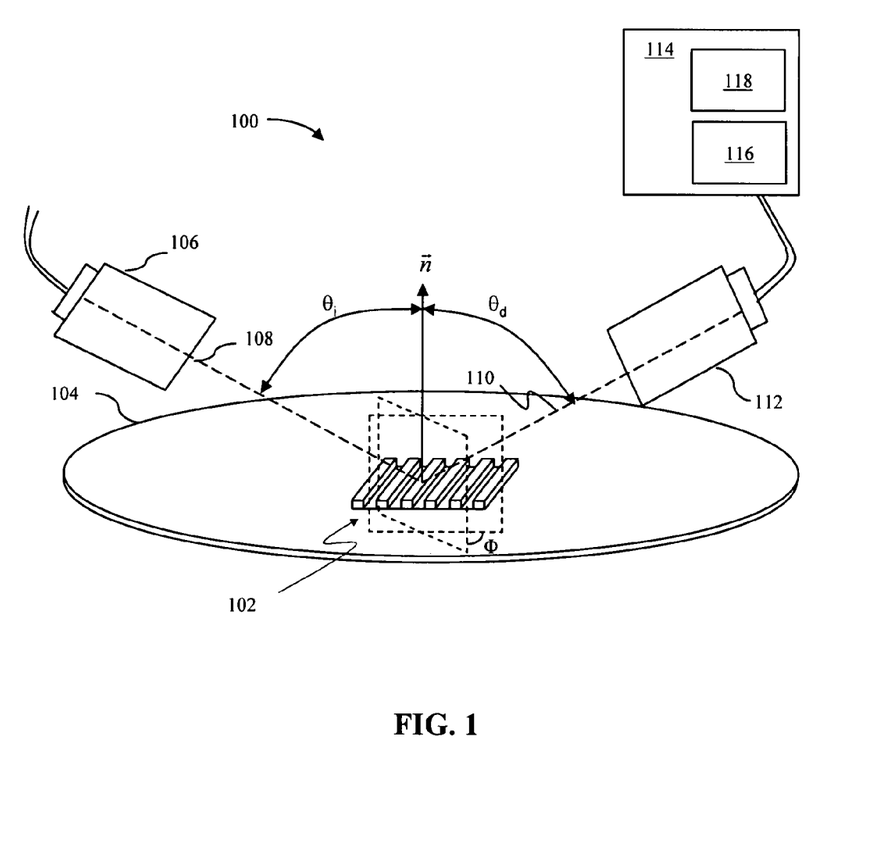
FIG. 1 depicts an exemplary optical metrology system.

With reference to FIG. 1, an optical metrology system 100 can be used to examine and analyze a structure. For example, optical metrology system 100 can be used to determine a feature of a periodic grating 102 formed on wafer 104. As described earlier, periodic grating 102 can be formed in test areas on wafer 104, such as adjacent to a device formed on wafer 104. Alternatively, periodic grating 102 can be formed in an area of the device that does not interfere with the operation of the device or along scribe lines on wafer 104.

As depicted in FIG. 1, optical metrology system 100 can include an optical metrology device with a source 106 and a detector 112. Periodic grating 102 is illuminated by an incident beam 108 from source 106. In the present exemplary embodiment, incident beam 108 is directed onto periodic grating 102 at an angle of incidence $\theta_i$ with respect to normal $\vec{n}$ of periodic grating 102 and an azimuth angle $\Phi$ (i.e., the angle between the plane of incidence beam 108 and the direction of the periodicity of periodic grating 102). Diffracted beam 110 leaves at an angle of $\theta_d$ with respect to normal $\vec{n}$ and is received by detector 112. Detector 112 converts the diffracted beam 110 into a measured diffraction signal, which can include reflectance, tan ($\Psi$), cos ($\Delta$), Fourier coefficients, and the like. It should be recognized, however, that incident beam 108 can be directed onto periodic grating 102 normal of periodic grating 102.

Optical metrology system 100 also includes a processing module 114 with a support vector machine 116. Processing module 114 is configured to receive the measured diffraction signal and determine one or more features of structure 102 using the measured diffraction signal and support vector machine 116.

Figure 2:
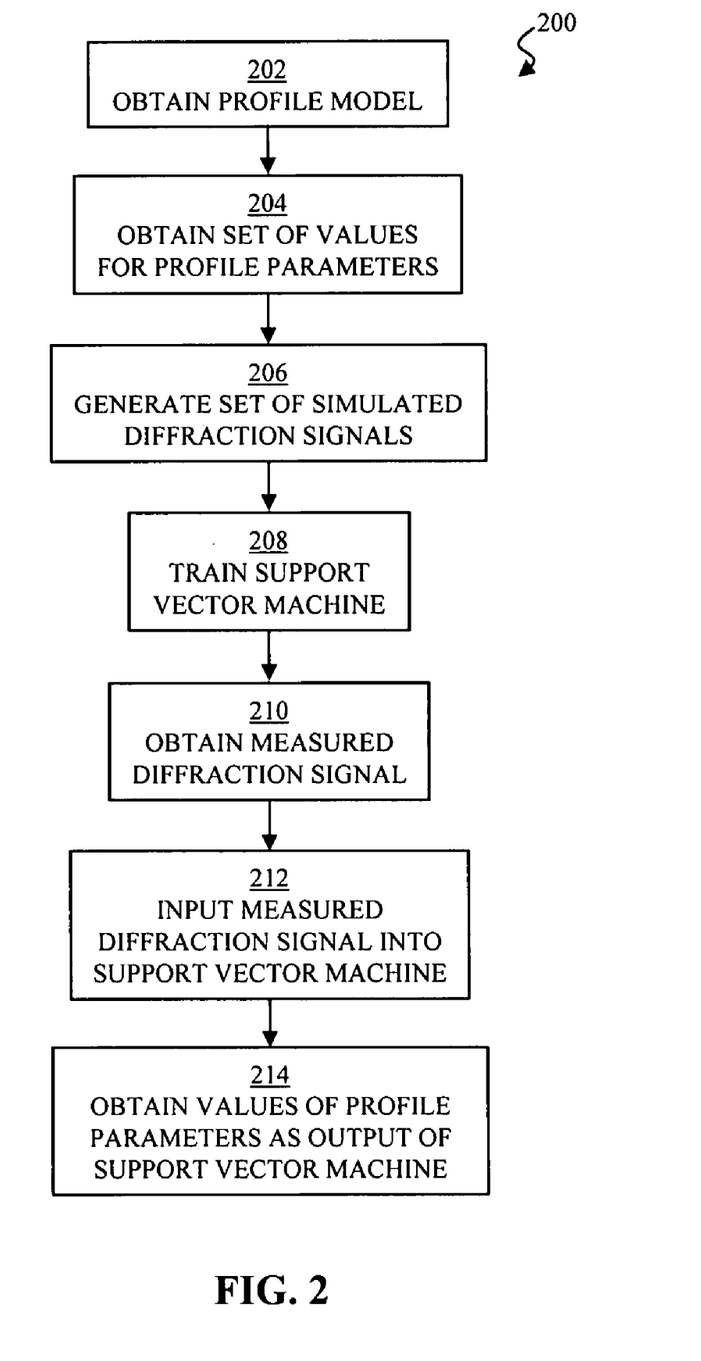
FIG. 2 depicts an exemplary process of examining a structure formed on a semiconductor wafer.

With reference to FIG. 2, an exemplary process 200 of determining one or more features of a structure formed on a semiconductor wafer is depicted. In step 202, a profile model of the structure is obtained. As described in greater detail below, the profile model is defined by profile parameters that characterize the geometric shape of the structure.

Figure 3A:
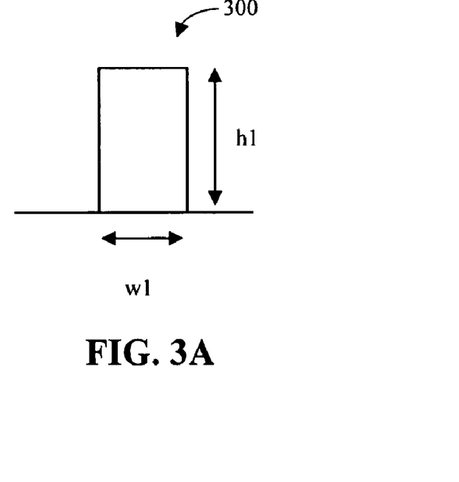
FIGS. 3A-3E depict exemplary profile models.
Figure 3B:
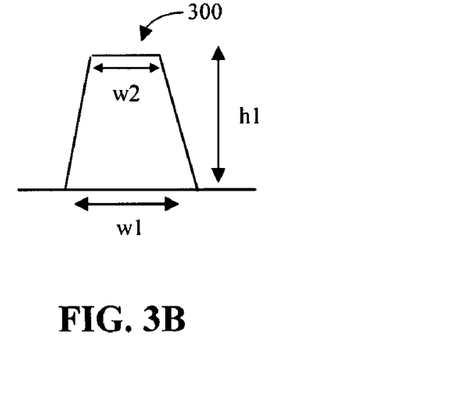
Figure 3C:
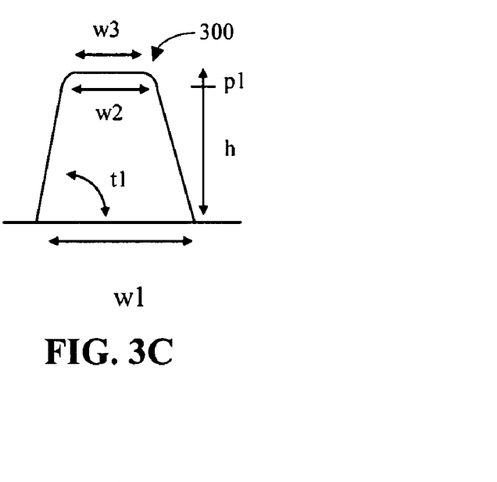
Figure 3D:
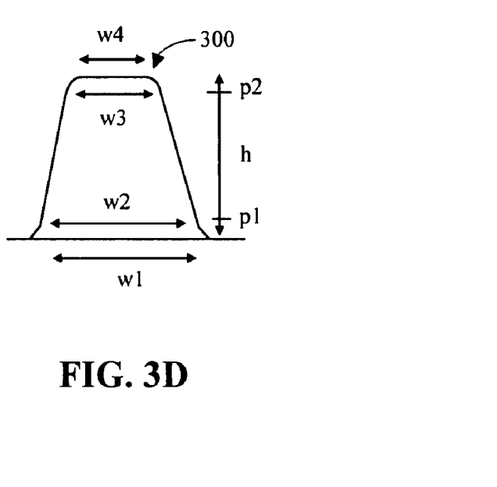
Figure 3E:
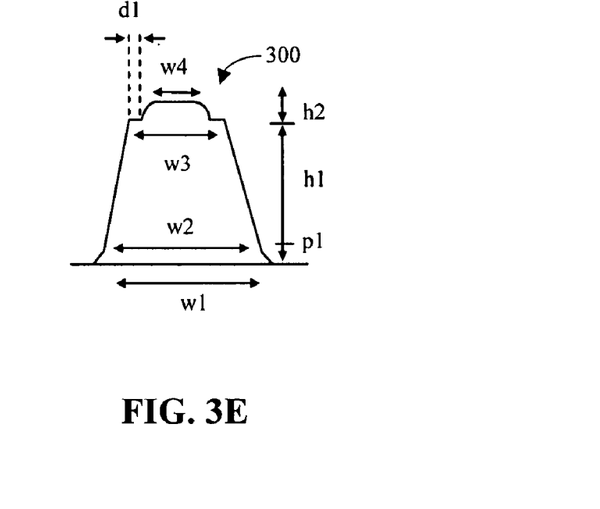

For example, as depicted in FIG. 3A, profile model 300 is defined by profile parameters h1 and w1 that define the height and width, respectively, of a structure. As depicted in FIGS. 3B to 3E, additional shapes and features of the structure can be characterized by increasing the number of profile parameters defining profile model 300. For example, as depicted in FIG. 3B, profile model 300 can be defined by profile parameters h1, w1, and w2 that height, bottom width, and top width, respectively, of the structure. Note that the profile parameter w1 or w2 of profile model 300 can be referred to as the bottom critical dimension (CD) and top CD, respectively. It should be recognized that various types of profile parameters can be used to define profile model 300, including angle of incident (AOI), pitch, n & k, hardware parameters (e.g., polarizer angle), and the like.

Figure 4A:
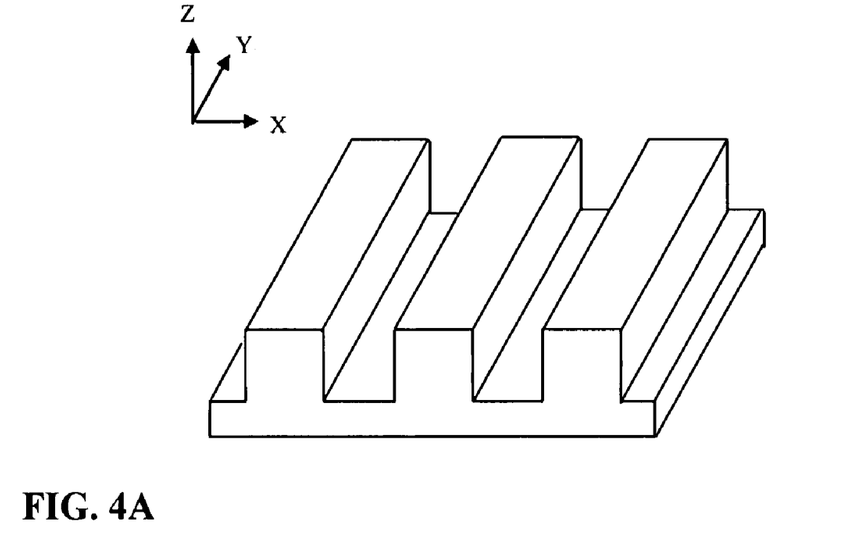
FIG. 4A depicts an exemplary one-dimension structure.

The term "one-dimension structure" is used herein to refer to a structure having a profile that varies in one dimension. For example, FIG. 4A depicts a periodic grating having a profile that varies in one dimension (i.e., the x-direction). The profile of the periodic grating depicted in FIG. 4A varies in the z-direction as a function of the x-direction. However, the profile of the periodic grating depicted in FIG. 4A is assumed to be substantially uniform or continuous in the y-direction.

Figure 4B:
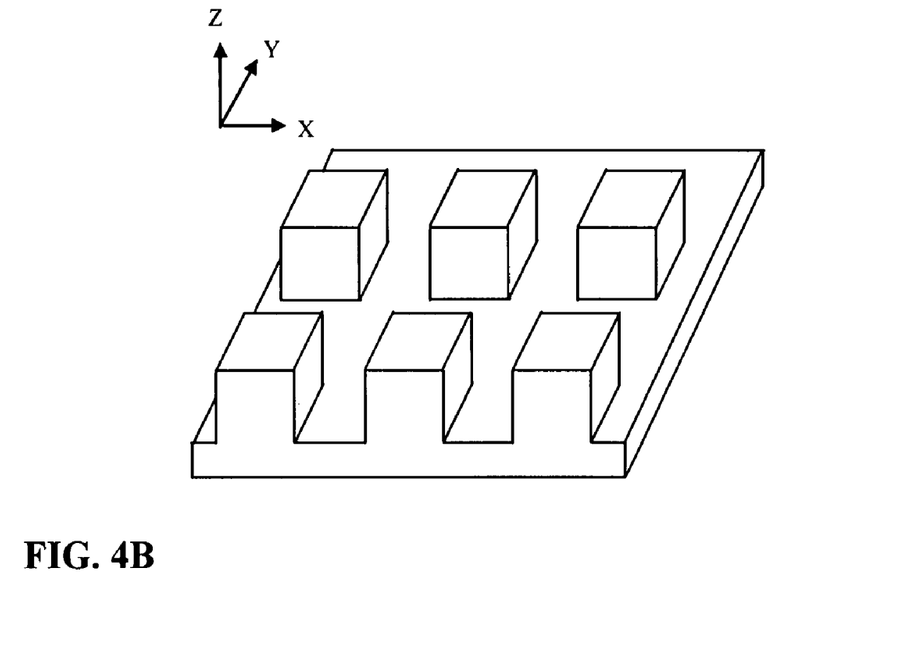
FIG. 4B depicts an exemplary two-dimension structure.

The term "two-dimension structure" is used herein to refer to a structure having a profile that varies in two-dimensions. For example, FIG. 4B depicts a periodic grating having a profile that varies in two dimensions (i.e., the x-direction and the y-direction). The profile of the periodic grating depicted in FIG. 4B varies in the z-direction.

Figure 5A:
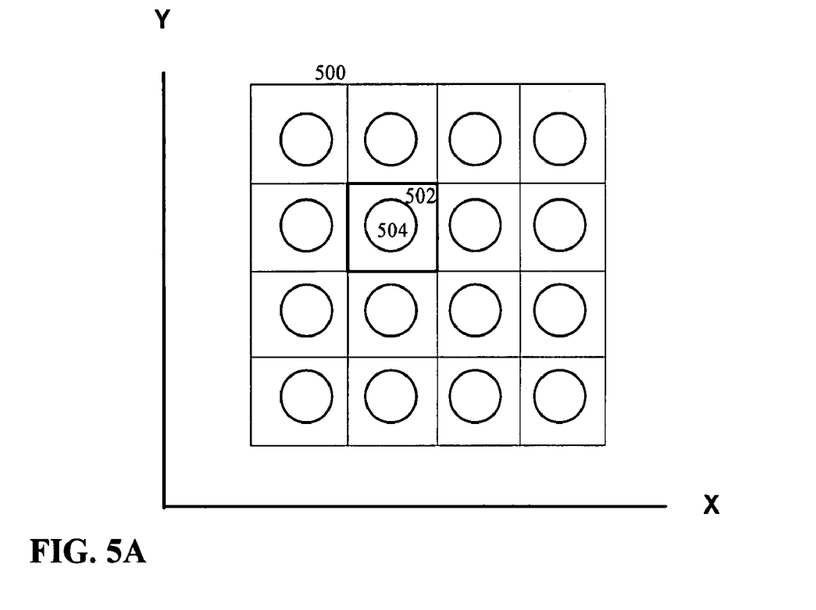
FIGS. 5A, 5B, and 5C depict exemplary profile models of two-dimension structures.

FIG. 5A depicts a top-view of exemplary orthogonal grid of unit cells of a two-dimension repeating structure. A hypothetical grid of lines is superimposed on the top-view of the repeating structure where the lines of the grid are drawn along the direction of periodicity. The hypothetical grid of lines forms areas referred to as unit cells. The unit cells may be arranged in an orthogonal or non-orthogonal configuration. Two-dimension repeating structures may comprise features such as repeating posts, contact holes, vias, islands, or combinations of two or more shapes within a unit cell. Furthermore, the features may have a variety of shapes and may be concave or convex features or a combination of concave and convex features. Referring to FIG. 5A, the repeating structure 500 comprises unit cells with holes arranged in an orthogonal manner. Unit cell 502 includes all the features and components inside the unit cell 502, primarily comprising a hole 504 substantially in the center of the unit cell 502.

Figure 5B:
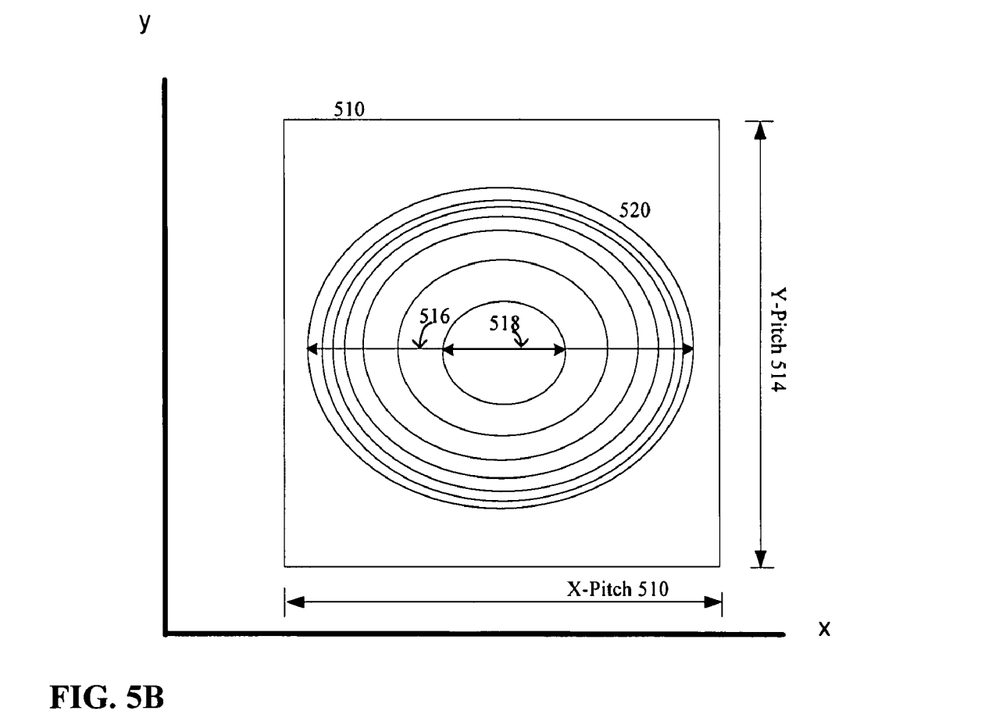

FIG. 5B depicts a top-view of a two-dimension repeating structure. Unit cell 510 includes a concave elliptical hole. FIG. 5B shows a unit cell 510 with a feature 520 that comprises an elliptical hole wherein the dimensions become progressively smaller until the bottom of the hole. Profile parameters used to characterize the structure includes the X-pitch 510 and the Y-pitch 514. In addition, the major axis of the ellipse 516 that represents the top of the feature 520 and the major axis of the ellipse 518 that represents the bottom of the feature 520 may be used to characterize the feature 520. Furthermore, any intermediate major axis between the top and bottom of the feature may also be used as well as any minor axis of the top, intermediate, or bottom ellipse, (not shown).

Figure 5C:
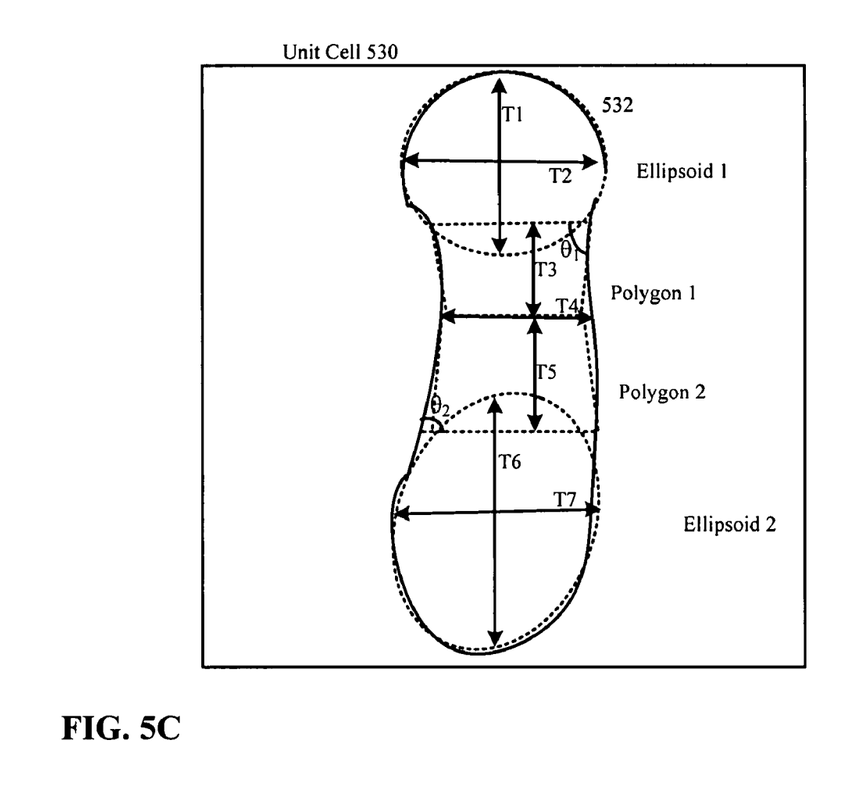

FIG. 5C is an exemplary technique for characterizing the top-view of a two-dimension repeating structure. A unit cell 530 of a repeating structure is a feature 532, an island with a peanut-shape viewed from the top. One modeling approach includes approximating the feature 532 with a variable number or combinations of ellipses and polygons. Assume further that after analyzing the variability of the top-view shape of the feature 522, it was determined that two ellipses, Ellipsoid 1 and Ellipsoid 2, and two polygons, Polygon 1 and Polygon 2 were found to fully characterize feature 532. In turn, parameters needed to characterize the two ellipses and two polygons comprise nine parameters as follows: T1 and T2 for Ellipsoid 1; T3, T4, and $\theta_1$ for Polygon 1; T4. T5, and $\theta_2$ for Polygon 2; T6 and T7 for Ellipsoid 2. Many other combinations of shapes could be used to characterize the top-view of the feature 532 in unit cell 530. For a detailed description of modeling two-dimension repeating structures, refer to U.S. patent application Ser. No. 11/061,303, OPTICAL METROLOGY OPTIMIZATION FOR REPETITIVE STRUCTURES, by Vuong, et al., filed on Apr. 27, 2004, and is incorporated in its entirety herein by reference.

In one embodiment, correlations between profile parameters are determined. The profile parameters used to define the profile model are selected based on the determined correlations. In particular, the profile parameters having correlations below a desired amount of correlation are selected. Multivariate analysis can be used to determine the correlations of profile parameters. Multivariate analysis can include a linear analysis or a nonlinear analysis. Additionally, multivariate analysis can include Principal Components Analysis (PCA), Independent Component Analysis, Cross Correlation Analysis, Linear Approximation Analysis, and the like. For a detailed description of a method of determining correlations of multiple profile parameters, refer to U.S. patent application Ser. No. 11/349,773, TRANSFORMING METROLOGY DATA FROM A SEMICONDUCTOR TREATMENT SYSTEM USING MULTIVARIATE ANALYSIS, by Vuong, et al., filed on May 8, 2006, and is incorporated in its entirety herein by reference.

In step 204, a set of values for the profile parameters is obtained. The values for the profile parameters in the set can be determined either empirically or through experience. For example, if the top width (i.e., top CD) of the structure to be examined is expected to vary within a range of values, then a number of different values within the range of values is used as the set obtained in step 204. For example, assume top CD is expected to vary within a range of 30 nanometers, such as between 80 nanometers and 110 nanometers. A number of different values of top CD within the range of 80 nanometers and 110 nanometers are used as the set of values for the profile parameters in step 204.

In step 206, a set of simulated diffraction signals is generated using the set of values for the profile parameters. Each simulated diffraction signal characterizing the behavior of light diffracted from the structure. In one exemplary embodiment, the simulated diffraction signal can be generated by calculating the simulated diffraction signal using a numerical analysis technique, such as rigorous coupled-wave analysis, with the profile parameters as inputs. In another exemplary embodiment, the simulated diffraction signal can be generated using a machine learning algorithm, such as back-propagation, radial basis function, support vector, kernel regression, and the like. For more detail, see U.S. Pat. No. 6,913, 900, entitled GENERATION OF A LIBRARY OF PERIODIC GRATING DIFFRACTION SIGNAL, by Niu, et al., issued on Sep. 13, 2005, and is incorporated in its entirety herein by reference.

In step 208, a support vector machine is trained using the set of simulated diffraction signals as inputs to the support vector machine and the set of values for the profile parameters as expected outputs of the support vector machine. Using the set of simulated diffraction signals as inputs and the set of values for the profile parameters as expected outputs, the support vector machine learns the function between the two sets. More specifically, in one exemplary embodiment, the support vector machine uses a kernel function to transfer the set of simulated diffraction signals, which has a non-linear relationship with the set of values for the profile parameters, to a feature space, which has a linear relationship to the set of values for the profile parameters. See, Lipo Wang, "Support Vector Machine—An introduction" Support Vector Machines: Theory and Applications, pages 1-45 (2005).

The accuracy of the support vector machine is typically improved by increasing the number of simulated diffraction signals and values for the profile parameters used in the training process. To increase the speed of the training process, a sequential minimal optimization process can be used. See, Platt, John C., "Fast Training of Support Vector Machines using Sequential Minimal Optimization," Advances in kernel methods: support vector learning, pages 185-208 (1999).

In one exemplary embodiment, after the training process, the support vector machine can be tested using a test set of simulated diffraction signals and a test set of values for profile parameters. More specifically, a test set of values for profile parameters is obtained. Preferably the values for the profile parameters in the test set are different than the values used in the set used for training. However, the values used in the test set are within the range of values used for training. The test set of simulated diffraction signals is generated using the test set of values for profile parameters. The test set of simulated diffraction signals is inputted into the support vector machine to generate an output set of values for profile parameters. The output set is then compared to the test set of values for profile parameters to determine accuracy of the support vector machine.

Figure 6A:
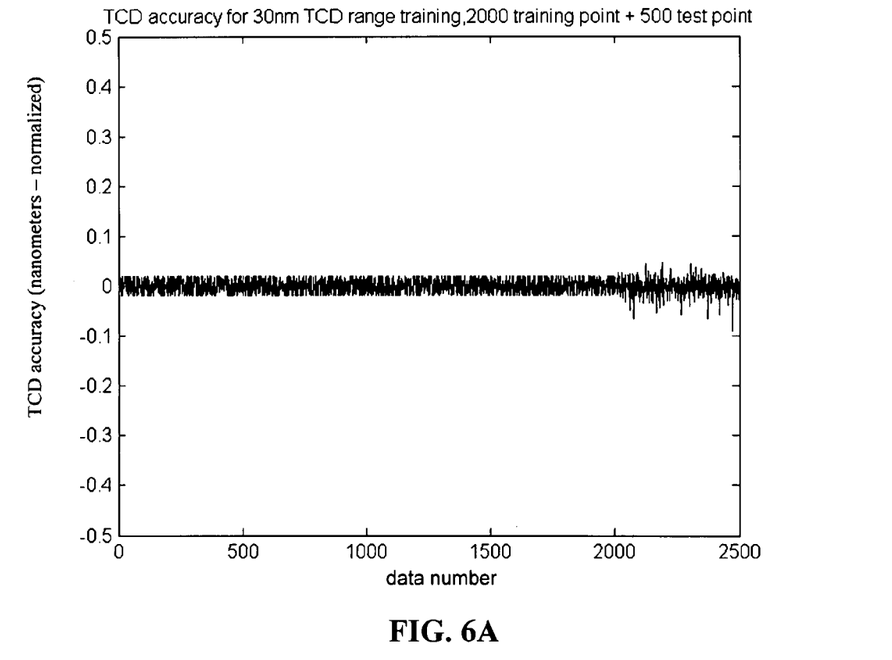
FIGS. 6A, 6B, and 6C depict graphs of accuracies of support vector machines.
Figure 6B:
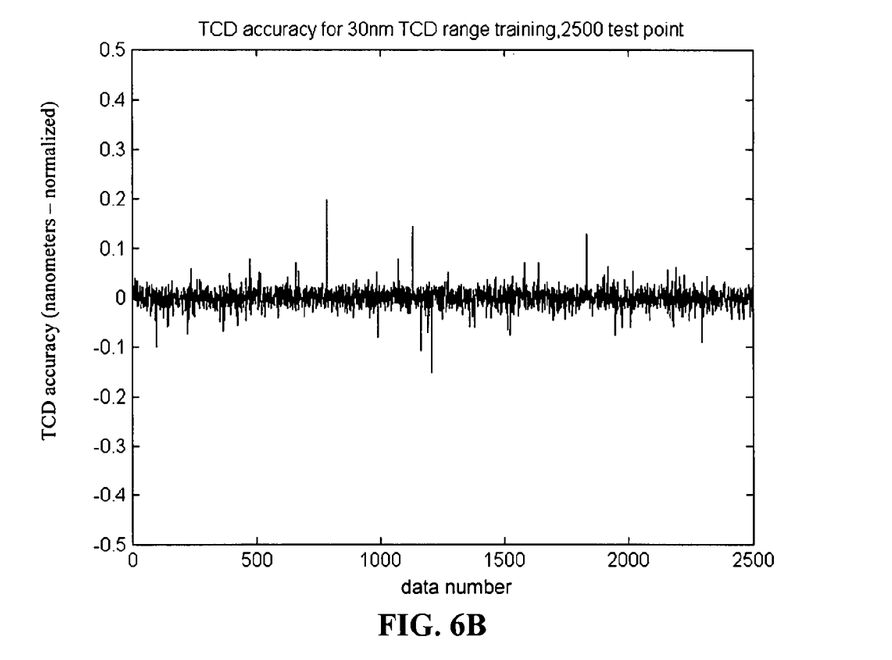

FIGS. 6A and 6B are graphs depicting the accuracy of a support vector machine trained using 2,000 training points (i.e., 2,000 values for profile parameters in the set used for training and 2,000 simulated diffraction signals in the set used for training) for a top CD range of 30 nanometers. The accuracy depicted in FIGS. 6A and 6B is determined as the difference between the expected value of top CD, which is the top CD value corresponding to the simulated diffraction signal used as the input to the support vector machine, and the value of top CD generated as an output of the support vector machine. In FIG. 6A, 500 test points were used to test the accuracy of the support vector machine. In FIG. 6B, 2500 test points were used to test the accuracy of the support vector machine.

If the accuracy of the support vector machine does not meet one or more accuracy criteria during the testing process, the support vector machine can be retrained. In one exemplary embodiment, the support vector machine can be retrained using one or more of the simulated diffraction signals and values for profile parameters used in the testing process.

For example, with reference to FIG. 6B, several test points are depicted as exceeding 0.1 and −0.1 nanometers as normalized values. Thus, if the accuracy criterion is that no test point can exceed 0.1 or −0.1 nanometers, then the support vector machine is retrained. In one exemplary embodiment, the values of profile parameters and the simulated diffraction signals corresponding to the test points that exceed 0.1 or −0.1 nanometers are used in retraining the support vector machine. It should be recognized that various accuracy criteria can be used to determine if the support vector machine is to be retrained. For example, a maximum number of test points exceeding 0.1 or −0.1 nanometers can be used as the accuracy criterion.

Figure 6C:
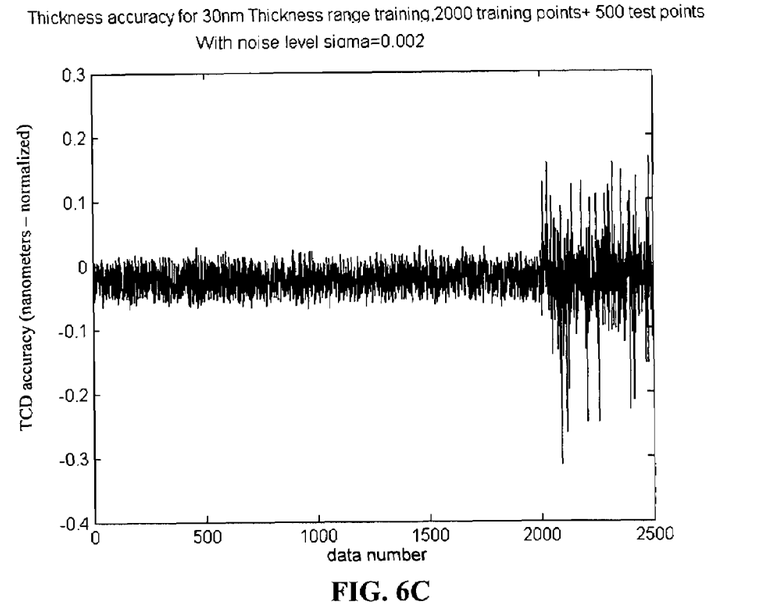

In one exemplary embodiment, the testing process can include introducing a noise signal into the simulated diffraction signals used for testing. For example, FIG. 6C depicts 500 test points with a noise level of 0.002 (sigma) introduced into the simulated diffraction signals of the test set. The accuracy depicted in FIG. 6C is determined as the difference between the expected value of top CD, which is the top CD value corresponding to the simulated diffraction signal used as the input to the support vector machine, and the value of top CD generated as an output of the support vector machine. The accuracy values in FIG. 6C are normalized values.

After the support vector machine has been trained, tested, and/or retrained, one or more features of a structure can be determined using the support vector machine. In particular, in step 210, a measured diffraction signal off the structure is obtained. After the support vector machine has been trained, in step 212, the measured diffraction signal is inputted into the trained support vector machine. In step 214, after step 212, values of profile parameters of the structure are obtained as an output from the trained support vector machine.

Figure 7:
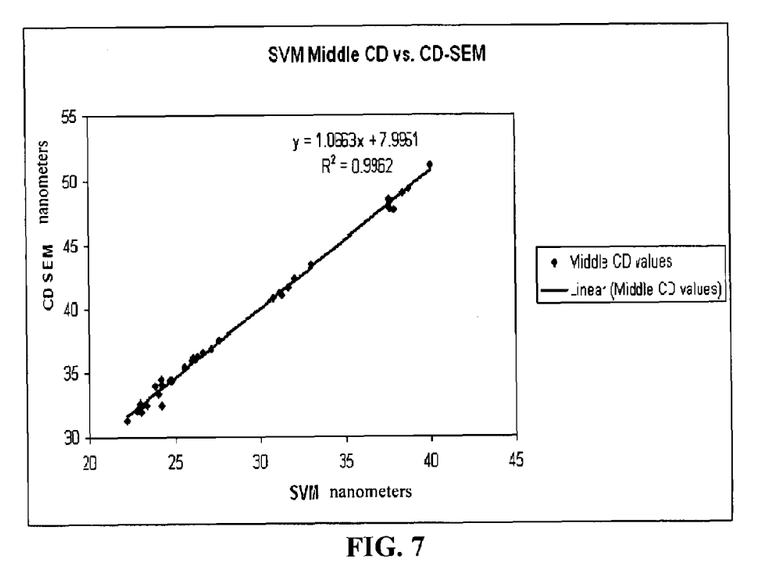
FIG. 7 depicts a comparison of results of using a support vector machine and a critical dimension-scanning electron microscope (CD-SEM)

FIG. 7 depicts a graph comparing results obtained from using a support vector machine and a CD-scanning electron microscope (CD-SEM) to determine a feature of a structure (in this example, middle CD). In particular, the horizontal axis corresponds to values of middle CD determined using the support vector machine. The vertical axis corresponds to values of middle CD determined using the CD-SEM. The values of the middle CD are provided in nanometers and are not normalized. As shown in FIG. 7, the results had an $R^2$ value of 0.9962.

In one exemplary embodiment, the values of profile parameters are normalized values. More specifically, the values for the profile parameters obtained in step 204 are normalized. The support vector machine is trained in step 208 using the normalized values for the profile parameters. Thus, the values of profile parameters obtained as an output from the trained support vector machine in step 214 are normalized values. In the present exemplary embodiment, the normalized values obtained in step 214 are then de-normalized.

In one exemplary embodiment, the simulated diffraction signals are defined using a standard set of signal parameters. The standard set includes a reflectance parameter, which characterizes the change in intensity of light when reflected on the structure, and a polarization parameter, which characterizes the change in polarization states of light when reflected on the structure.

In the present exemplary embodiment, the reflectance parameter (R) of the standard set of signal parameters corresponds to an average of the square of the absolute value of the complex reflection coefficients of the light. The polarization parameter includes a first parameter (N) that characterizes half of the difference between the square of the absolute value of the complex reflection coefficients normalized to R, a second parameter (S) that characterizes the imaginary component of the interference of the two complex reflection coefficients normalized to R, and a third parameter (C) that characterizes the real component of the interference of the two complex reflection coefficients normalized to R. Thus, the standard set of signal parameters includes the parameters (R, NSC).

In the present exemplary embodiment, the simulated diffraction signals generated in step 206 are defined using the standard set of signal parameters (R, NSC). The support vector machine is trained in step 208 using simulated diffraction signals defined using the standard set of signal parameter (R, NSC). When the measured diffraction signal is measured using a reflectometer that only measures the change in the intensity of light, such as a spectrometer reflectometer, processing module 114 uses only the reflectance parameter of the standard set of signal parameters. When the measured diffraction signal is measured using an ellipsometer that measures both the change in the intensity of light and polarization states of light, such as a rotating compensator ellipsometer (RCE), processing module 114 uses the reflectance parameter and the polarization parameter of the standard set of signal parameters.

Figure 8:
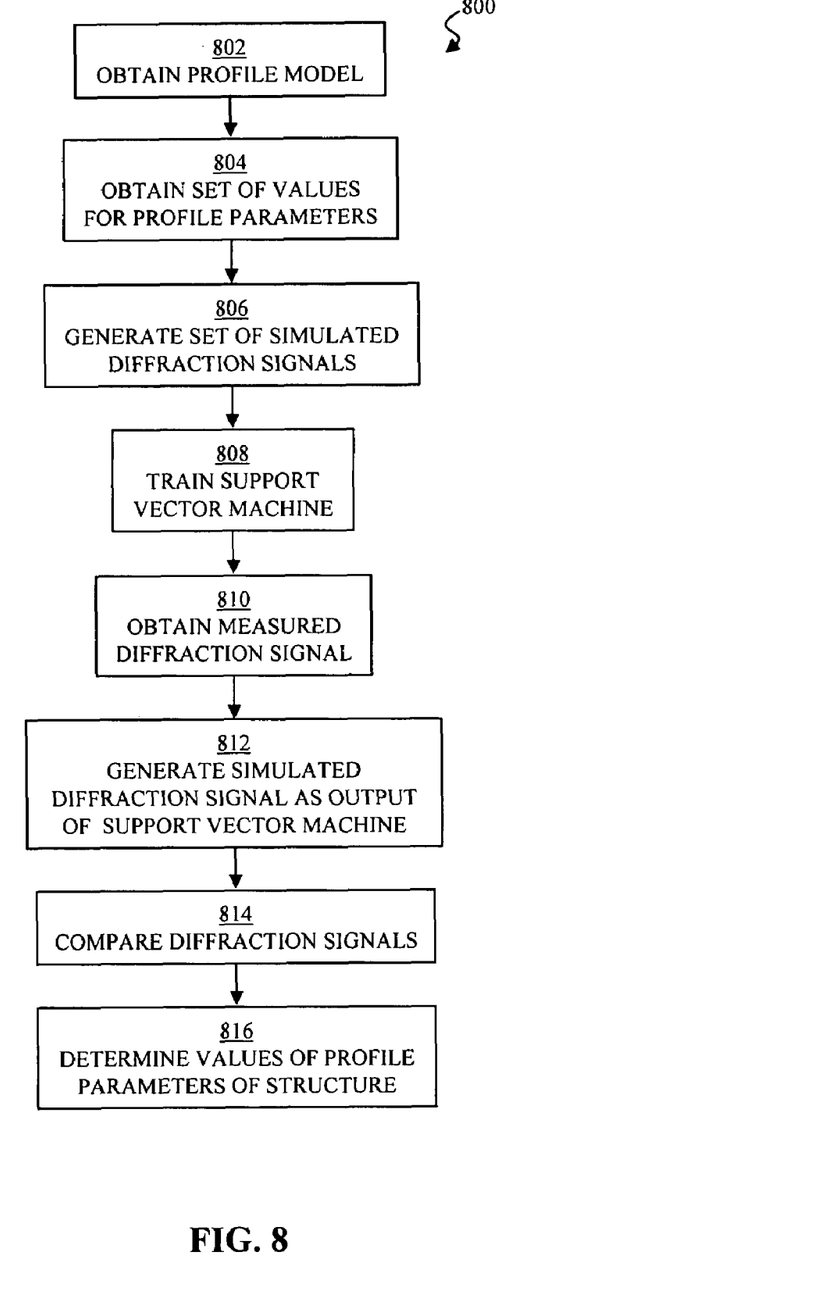
FIG. 8 depicts another exemplary process of examining a structure on a semiconductor wafer.

With reference to FIG. 8, an exemplary process 800 of determining one or more features of a structure formed on a semiconductor wafer is depicted. In step 802, a profile model of the structure is obtained. As described above, the profile model is defined by profile parameters that characterize the geometric shape of the structure. In step 804, a training set of values for the profile parameters is obtained. In step 806, a training set of simulated diffraction signals is generated using the training set of values for the profile parameters. As described above, each simulated diffraction signal characterizing the behavior of light diffracted from the structure. In step 808, a support vector machine is trained using the training set of values for the profile parameters as inputs to the support vector machine and the training set of simulated diffraction signals as expected outputs of the support vector machine.

As described above, after the training process, the support vector machine can be tested using a test set of simulated diffraction signals and a test set of values for profile parameters. As also described above, if the accuracy of the support vector machine does not meet one or more accuracy criteria during the testing process, the support vector machine can be retrained.

After the support vector machine has been trained, tested, and/or retrained, one or more features of a structure can be determined using the support vector machine. In particular, in step 810, a measured diffraction signal off the structure is obtained. In step 812, a simulated diffraction signal is generated using a set of values for the profile parameters as inputs to the trained support vector machine. In step 814, the measured diffraction signal is compared to the simulated diffraction signal generated in 812. When the measured diffraction signal and simulated diffraction signal match within one or more matching criteria, values of profile parameters of the structure are determined to be the set of values for the profile parameters used in step 812 to generate the simulated diffraction signal.

As described above, in one exemplary embodiment, the values of profile parameters are normalized values. As also described above, in one exemplary embodiment, the simulated diffraction signals are defined using a standard set of signal parameters (R, NSC).

In one exemplary embodiment, in step 812, a plurality of simulated diffraction signals is generated using different sets of values for the profile parameters as inputs to the trained support vector machine. Each simulated diffraction signal is associated with the set of values for the profile parameters used to generate the simulated diffraction signal. The plurality of simulated diffraction signals, the different sets of values for the profile parameters, and the association between each simulated diffraction signal with the set of values for the profile parameters used to generate the simulated diffraction signal are stored in a library 118 (FIG. 1).

In the present exemplary embodiment, when the measured diffraction signal and the simulated diffraction signal do not match within one or more matching criteria in step 814, the measured diffraction signal is compared with another simulated diffraction signal from the library 118 (FIG. 1) of simulated diffraction signals. When the measured diffraction signal and the another simulated diffraction signal match within one or more matching criteria, values of profile parameters of the structure are determined to be the set of values for the profile parameters associated with the simulated diffraction signal in the library 118 (FIG. 1).

In another exemplary embodiment, when the measured diffraction signal and the simulated diffraction signal do not match within one or more matching criteria in step 814, another simulated diffraction signal is generated using a set of different values for the profile parameters as inputs to the trained support vector machine. The measured diffraction signal is compared to the another simulated diffraction signal. When the measured diffraction signal and the another simulated diffraction signal match within one or more matching criteria, values of profile parameters of the structure are determined to be the set of different values for the profile parameters used to generate the another simulated diffraction signal.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching.

We claim:

1. A method of examining a structure formed on a semiconductor wafer, the method comprising:
    a) obtaining a profile model of the structure, the profile model being defined by profile parameters that characterize the geometric shape of the structure;
    b) obtaining a training set of values for the profile parameters;
    c) generating a training set of simulated diffraction signals using the training set of values for the profile parameters, each simulated diffraction signal characterizing the behavior of light diffracted from the structure, wherein the simulated diffraction signals in the training set of simulated diffraction signals are defined using a standard set of signal parameters comprising a reflectance parameter, which characterizes the change in intensity of light when reflected on the structure, and a polarization parameter, which characterizes the change in polarization states of light when reflected on the structure, wherein the polarization parameter comprises:
        a first polarization parameter that characterizes a difference between the square of the absolute value of complex reflection coefficients average over depolarization effects, and normalized to the reflectance parameter;
        a second polarization parameter that characterizes an imaginary component of an interference of the complex reflection coefficients average over depolarization effects, and normalized to the reflectance parameter; and
        a third polarization parameter that characterizes a real component of an interference of the complex reflection coefficients average over depolarization effects, and normalized to the reflectance parameter;
    d) training a support vector machine using the training set of values for the profile parameters as inputs to the support vector machine and the training set of simulated diffraction signals as expected outputs of the support vector machine;
    e) obtaining a measured diffraction signal off the structure, wherein the measured diffraction signal is defined using the standard set of signal parameters;
    f) generating a simulated diffraction signal using a set of values for the profile parameters as inputs to the trained support vector machine, wherein the simulated diffraction signal is defined using the standard set of signal parameters;
    g) comparing the measured diffraction signal to the simulated diffraction signal generated in f); and
    h) when the measured diffraction signal and simulated diffraction signal match within one or more matching criteria, determining values of profile parameters of the structure to be the set of values for the profile parameters used in f) to generate the simulated diffraction signal.

2. The method of claim 1, wherein f) comprises:
generating a plurality of simulated diffraction signals using different sets of values for the profile parameters as inputs to the trained support vector machine, wherein each simulated diffraction signal is associated with the set of values for the profile parameters used to generate the simulated diffraction signal; and
storing the plurality of simulated diffraction signals, the different sets of values for the profile parameters, and the association between each simulated diffraction signal with the set of values for the profile parameters used to generate the simulated diffraction signal in a library.

3. The method of claim 2, wherein when the measured diffraction signal and the simulated diffraction signal do not match within one or more matching criteria in g),
comparing the measured diffraction signal with another simulated diffraction signal from the library of simulated diffraction signals; and
when the measured diffraction signal and the another simulated diffraction signal match within one or more matching criteria, determining values of profile parameters of the structure to be the set of values for the profile parameters associated with the simulated diffraction signal in the library.

4. The method of claim 1, when the measured diffraction signal and the simulated diffraction signal do not match within one or more matching criteria in g):
generating another simulated diffraction signal using a set of different values for the profile parameters as inputs to the trained support vector machine;
comparing the measured diffraction signal to the another simulated diffraction signal; and
when the measured diffraction signal and the another simulated diffraction signal match within one or more matching criteria, determining values of profile parameters of the structure to be the set of different values for the profile parameters used to generate the another simulated diffraction signal.

5. The method of claim 1, further comprising:
normalizing values of profile parameters, wherein the training set of simulated diffraction signals are generated using the normalized values of profile parameters; and
de-normalizing the values of profile parameter obtained in g).

6. The method of claim 1, wherein the training set of simulated diffraction signals is generated using a modeling technique.

7. The method of claim 6, wherein the modeling technique includes rigorous coupled wave analysis, integral method, Fresnel method, finite analysis, or modal analysis.

8. The method of claim 1, further comprising:
determining correlations for profile parameters; and
selecting the profile parameters used to define the profile model in a) based on the determined correlations.

9. The method of claim 1, wherein the support vector machine is trained in d) using sequential minimal optimization.

10. The method of claim 1, after d) and before e):
obtaining a test set of simulated diffraction signals and a test set of values for profile parameters;
testing the support vector machine using the test set of simulated diffraction signals as inputs to the support vector machine and the test set of values for profile parameters as expected outputs of the support vector machine; and
if one or more accuracy criteria are not met, retraining the support vector machine using one or more of the simulated diffraction signals in the test set and one or more values for profile parameters in the test set.

11. The method of claim 10, further comprising:
inserting a noise signal into the simulated diffraction signals in the test set before testing the support vector machine.

12. A computer-readable storage medium containing computer executable instructions for causing a computer to determine one or more features of a structure formed on a semiconductor wafer, comprising instructions for:
a) obtaining a profile model of the structure, the profile model being defined by profile parameters that characterize the geometric shape of the structure;
b) obtaining a training set of values for the profile parameters;
c) generating a training set of simulated diffraction signals using the training set of values for the profile parameters, each simulated diffraction signal characterizing the behavior of light diffracted from the structure, wherein the simulated diffraction signals in the training set of simulated diffraction signals are defined using a standard set of signal parameters comprising a reflectance parameter, which characterizes the change in intensity of light when reflected on the structure, and a polarization parameter, which characterizes the change in polarization states of light when reflected on the structure, wherein the polarization parameter comprises:
a first polarization parameter that characterizes a difference between the square of the absolute value of complex reflection coefficients average over depolarization effects, and normalized to the reflectance parameter;
a second polarization parameter that characterizes an imaginary component of an interference of the complex reflection coefficients average over depolarization effects, and normalized to the reflectance parameter; and
a third polarization parameter that characterizes a real component of an interference of the complex reflection coefficients average over depolarization effects, and normalized to the reflectance parameter;
d) training a support vector machine using the training set of values for the profile parameters as inputs to the support vector machine and the training set of simulated diffraction signals as expected outputs of the support vector machine;
e) obtaining a measured diffraction signal off the structure, wherein the measured diffraction signal is defined using the standard set of signal parameters;
f) generating a simulated diffraction signal using a set of values for the profile parameters as inputs to the trained support vector machine, wherein the simulated diffraction signal is defined using the standard set of signal parameters;
g) comparing the measured diffraction signal to the simulated diffraction signal generated in f); and
h) when the measured diffraction signal and simulated diffraction signal match within one or more matching criteria, determining values of profile parameters of the structure to be the set of values for the profile parameters used in f) to generate the simulated diffraction signal.

13. The computer-readable storage medium of claim 12, wherein f) comprises instructions for:
- generating a plurality of simulated diffraction signals using different sets of values for the profile parameters as inputs to the trained support vector machine, wherein each simulated diffraction signal is associated with the set of values for the profile parameters used to generate the simulated diffraction signal; and
- storing the plurality of simulated diffraction signals, the different sets of values for the profile parameters, and the association between each simulated diffraction signal with the set of values for the profile parameters used to generate the simulated diffraction signal in a library.

14. The computer-readable storage medium of claim 13, wherein when the measured diffraction signal and the simulated diffraction signal do not match within one or more matching criteria in g):
- comparing the measured diffraction signal with another simulated diffraction signal from the library of simulated diffraction signals; and
- when the measured diffraction signal and the another simulated diffraction signal match within one or more matching criteria, determining values of profile parameters of the structure to be the set of values for the profile parameters associated with the simulated diffraction signal in the library.

15. The computer-readable storage medium of claim 12, when the measured diffraction signal and the simulated diffraction signal do not match within one or more matching criteria in g):
- generating another simulated diffraction signal using a set of different values for the profile parameters as inputs to the trained support vector machine;
- comparing the measured diffraction signal to the another simulated diffraction signal; and
- when the measured diffraction signal and the another simulated diffraction signal match within one or more matching criteria, determining values of profile parameters of the structure to be the set of different values for the profile parameters used to generate the another simulated diffraction signal.

16. The computer-readable storage medium of claim 12, further comprising instructions for:
- normalizing values of profile parameters, wherein the training set of simulated diffraction signals are generated using the normalized values of profile parameters; and
- de-normalizing the values of profile parameter obtained in g).

17. The computer-readable storage medium of claim 12, further comprising instructions for:
- determining correlations for profile parameters; and
- selecting the profile parameters used to define the profile model in a) based on the determined correlations.

18. The computer-readable storage medium of claim 12, wherein the support vector machine is trained in d) using sequential minimal optimization.

19. The computer-readable storage medium of claim 12, after d) and before e):
- obtaining a test set of simulated diffraction signals and a test set of values for profile parameters;
- testing the support vector machine using the test set of simulated diffraction signals as inputs to the support vector machine and the test set of values for profile parameters as expected outputs of the support vector machine; and
- if one or more accuracy criteria are not met, retraining the support vector machine using one or more of the simulated diffraction signals in the test set and one or more values for profile parameters in the test set.

20. The computer-readable storage medium of claim 19, further comprising:
- inserting a noise signal into the simulated diffraction signals in the test set before testing the support vector machine.

21. A system to determine one or more features of a structure formed on a semiconductor wafer, comprising:
- an optical metrology device configured to measure a diffraction signal;
- a support vector machine, wherein the support vector machine is trained using a training set of values for profile parameters as inputs to the support vector machine and a training set of simulated diffraction signals as expected outputs of the support vector machine, wherein the training set of simulated diffraction signals is generated using the training set of values for the profile parameters, wherein the profile parameters characterize the geometric shape of the structure, wherein the simulated diffraction signals in the training set of simulated diffraction signals are defined using a standard set of signal parameters comprising a reflectance parameter, which characterizes the change in intensity of light when reflected on the structure, and a polarization parameter, which characterizes the change in polarization states of light when reflected on the structure, wherein the polarization parameter comprises:
  - a first polarization parameter that characterizes a difference between the square of the absolute value of complex reflection coefficients average over depolarization effects, and normalized to the reflectance parameter;
  - a second polarization parameter that characterizes an imaginary component of an interference of the complex reflection coefficients average over depolarization effects, and normalized to the reflectance parameter; and
  - a third polarization parameter that characterizes a real component of an interference of the complex reflection coefficients average over depolarization effects, and normalized to the reflectance parameter; and
- a processor configured to input a set of values for the profile parameters as inputs to the trained support vector machine, obtain a simulated diffraction signal as an output of the trained support vector machine, compare the simulated diffraction signal to the measured diffraction signal, and determine values of profile parameters of the structure used to generate the simulated diffraction signal when the measured diffraction signal and simulated diffraction signal match within one or more matching criteria.

* * * * *